United States Patent
Yuri et al.

(10) Patent No.: US 6,826,224 B2
(45) Date of Patent: Nov. 30, 2004

(54) HIGH-POWER SEMICONDUCTOR LASER ARRAY APPARATUS THAT OUTPUTS LASER LIGHTS MATCHED IN WAVELENGTH AND PHASE, MANUFACTURING METHOD THEREFOR, AND MULTI-WAVELENGTH LASER EMITTING APPARATUS USING SUCH HIGH-POWER SEMICONDUCTOR LASER ARRAY APPARATUS

(75) Inventors: Masaaki Yuri, Ibaraki (JP); Seiichiro Tamai, Osaka-fu (JP); Kunio Ito, Uji (JP); Masaru Kazumura, Takatsuki (JP)

(73) Assignee: Matsushita Electric Industrial Co., Ltd., Osaka-fu (JP)

(*) Notice: Subject to any disclaimer, the term of this patent is extended or adjusted under 35 U.S.C. 154(b) by 153 days.

(21) Appl. No.: 09/818,346

(22) Filed: Mar. 27, 2001

(65) Prior Publication Data

US 2001/0033590 A1 Oct. 25, 2001

(30) Foreign Application Priority Data

Mar. 27, 2000 (JP) ........................................ 2000-087459
Mar. 31, 2000 (JP) ........................................ 2000-099511
Mar. 31, 2000 (JP) ........................................ 2000-099514

(51) Int. Cl.$^7$ ............................. H01S 3/08; G02B 26/08
(52) U.S. Cl. ...................................... 372/108; 359/204
(58) Field of Search .............................. 372/43–50, 108; 359/204

(56) References Cited

U.S. PATENT DOCUMENTS

| | | | |
|---|---|---|---|
| 4,255,717 A | | 3/1981 | Scifres et al. .................. 372/50 |
| 4,266,549 A | | 5/1981 | Kimura ......................... 606/3 |
| RE31,806 E | * | 1/1985 | Scifres et al. .................. 372/50 |
| 4,541,712 A | | 9/1985 | Whitney ....................... 355/53 |
| 4,719,634 A | | 1/1988 | Streifer et al. ................ 372/46 |
| 4,903,274 A | | 2/1990 | Taneya et al. ................ 372/48 |
| 5,296,958 A | * | 3/1994 | Roddy et al. ................ 359/204 |
| 5,487,725 A | | 1/1996 | Peyman ........................ 604/22 |
| 5,713,892 A | | 2/1998 | Shimmick ..................... 606/5 |

FOREIGN PATENT DOCUMENTS

| | | | |
|---|---|---|---|
| DE | 42 34 342 | 4/1994 | .......... B25K/26/00 |
| DE | 33 30 293 | 3/1995 | .......... A61K/33/24 |
| EP | 0 301 846 | 2/1989 | ............. H01S/3/18 |
| EP | 0 450 668 | 10/1991 | ............. H01S/3/25 |
| EP | 0 625 846 | 11/1994 | ............ H04N/1/46 |
| JP | 560881993 | 4/1981 | ............. H01S/3/18 |

* cited by examiner

Primary Examiner—Quyen Leung

(57) ABSTRACT

A semiconductor laser array apparatus including: a substrate; a plurality of current blocking elements that are stripe shaped and are formed on the substrate; and a plurality of light waveguides that are formed between the plurality of current blocking elements, where at least two adjacent light waveguides are optically connected by removing a part of each current blocking element therebetween.

6 Claims, 14 Drawing Sheets

301

HIGH-POWER SEMICONDUCTOR LASER ARRAY APPARATUS THAT OUTPUTS LASER LIGHTS MATCHED IN WAVELENGTH AND PHASE, MANUFACTURING METHOD THEREFOR, AND MULTI-WAVELENGTH LASER EMITTING APPARATUS USING SUCH HIGH-POWER SEMICONDUCTOR LASER ARRAY APPARATUS

BACKGROUND OF THE INVENTION

1. Field of the Invention

The present invention relates to a high-power semiconductor laser array apparatus that is applicable to various fields, such as optical recording, optical communications, punching, and welding. The present invention also relates to a multi-wavelength laser emitting apparatus using a plurality of such semiconductor laser array apparatuses.

2. Description of the Related Art

In recent years, attempts have been made to apply semiconductor laser array apparatuses to various fields, such as optical recording, optical communications, punching, and welding. This creates demand for high-power semiconductor layer array apparatuses because currently available semiconductor laser array apparatuses are basically low-powered and are not applicable to these fields.

A high-power semiconductor laser array apparatus is disclosed by Japanese Laid-Open Patent Application No. H5-226765. The semiconductor laser array apparatus has an array structure where a plurality of semiconductor laser elements are formed on the same substrate. Note that in this specification, a semiconductor laser element refers to a laser oscillation unit including a current blocking layer.

In the semiconductor laser array apparatus, the semiconductor laser elements are arranged close to each other in the width direction thereof. This arrangement causes interference between laser lights emitted from the semiconductor laser elements, so that the laser lights are matched in wavelength and phase (so-called "phase locking" is achieved). As a result, the laser lights emitted from the plurality of semiconductor laser elements are condensed to form a spot and the output power of the semiconductor laser array apparatus is increased.

To increase the flexibility in designing a semiconductor laser apparatus, it is required to develop a new structure where the phase locking is achieved without arranging the semiconductor laser elements close to each other in the width direction.

Gas lasers (such as $CO_2$ lasers and excimer lasers) and solid lasers (such as YAG lasers) are mainly used for industrial laser emitting apparatuses that are applied, for instance, to welding and punching because these lasers have high output powers.

A laser emitting apparatus using a gas laser or a solid laser, however, inevitably increases in size due to its structure. In particular, a laser emitting apparatus using a gas laser needs to be equipped with a gas cylinder, so that the hardware scale of the laser emitting apparatus becomes large even if it is designed to process small materials. This increases the price of the laser emitting apparatus and creates a necessity for a large installation space. Also, the laser emitting apparatus consumes a large amount of electricity due to its low luminous efficiency. Further, because the gas cylinder of the laser emitting apparatus needs to be refilled, the maintenance cost is increased.

Also, the recent development in the material industry has realized various new types of works (materials to be processed using lasers). This causes a problem that the laser emitting apparatus using a gas laser or a solid laser cannot process a work produced by mixing two types of materials having different absorption coefficients for a laser of a wavelength.

The laser light emitted from a gas laser or a solid laser has a specific wavelength and it is difficult to change the wavelength. Suppose that a work has been produced from materials A and B, the material A has a high absorption coefficient for a laser light of a wavelength $\alpha$, and the material B has a low absorption coefficient for the laser light. In this case, it is necessary to increase a laser power to melt the material B as well. This excessively raises the temperature of the material A and thus melts unnecessary parts of the material A. Therefore, if a hole is formed in the work, the diameter of the hole becomes larger than an intended size. This results in a problem that the processing accuracy is significantly impaired.

To cope with this problem, it is preferred to also use a laser light of a wavelength $\beta$, for which the material B has a high absorption coefficient. However, this is not a feasible solution because, as described above, it is difficult to change the wavelength of the laser light emitted from a multi-wavelength laser emitting apparatus using a gas laser or a solid laser.

Also in various other fields, there is demand for a multi-wavelength laser emitting apparatus of a reduced size but a high output power.

SUMMARY OF THE INVENTION

The first object of the present invention is therefore to provide a semiconductor laser array apparatus where laser lights emitted from a plurality of elements provided on the same substrate are matched in wavelength and phase (that is, the laser lights are phase locked).

The second object of the present invention is to provide a multi-wavelength laser emitting apparatus that realizes a small-sized but relatively high-power laser appliance which emits various laser lights having different wavelengths.

The first object is achieved by a semiconductor laser array apparatus including: a substrate; a plurality of current blocking elements that are stripe shaped and are formed on the substrate; and a plurality of light waveguides that are formed between the plurality of current blocking elements, where at least two adjacent light waveguides are optically connected by removing a part of each current blocking element therebetween.

This construction allows the semiconductor laser array apparatus to match emitted laser lights in wavelength and phase (that is, the laser lights are phase locked) without arranging semiconductor laser elements close to each other in the width direction thereof on the same substrate.

With the conventional technique described above, laser elements need to be arranged close to each other in an arrangement direction of light waveguides to cause interference between laser lights emitted from the laser elements. This limits the width of a current blocking layer and decreases design flexibility. Also, because the laser elements are arranged close to each other, heat is confined in a narrow space and the amount of generated heat is increased. Temperature is increased particularly in a center area and the reliability of an apparatus is reduced.

On the other hand, with the technique of the present invention, semiconductor laser elements are not arranged close to each other in the width direction thereof on the same substrate. This increases design flexibility and reduces the amount of heat generated at each laser element. As a result, the reliability of the apparatus is increased.

Also, because semiconductor laser elements are not arranged close to each other on the same substrate with the technique of the present invention, phase locking is achieved with reliability, in comparison with the conventional technique. That is, with the conventional technique where phase locking is achieved by arranging semiconductor laser elements close to each other, the phase locking cannot be achieved with reliability. However, with the technique of the present invention where light waveguides are optically connected to each other by discontinuous areas of the current blocking layer, light distribution areas are formed also in the discontiguous areas. These light distribution areas cause the interference between lights traveling through adjacent light waveguides, and thus amplify the lights. This makes it possible that phase locking is achieved with stability and reliability.

Here, the discontiguous areas of the current blocking layer may be long grooves and arranged close to the light waveguides. In this case, phase locking can be achieved without problems. This is because even if the discontiguous areas are not connected to the light waveguides, waveguide areas through which lights seep overlap the light distribution areas. Therefore, interference is caused between lights traveling through adjacent light waveguides (that is "a light interference function" is achieved) and phase locking is provided.

Also, the discontiguous areas of the current blocking layer may be long grooves and formed as connection waveguides that connect the light waveguides. In this case, although light loss is caused due to the scattering of lights, phase locking is achieved with more reliability. With this construction where the discontiguous areas of the current blocking layer are formed as the connection waveguides, lights traveling through the light waveguides are scattered and introduced into the connection waveguides. Therefore, lights in the light waveguides travel also through the adjacent waveguides. This achieves the light interference function and a function of sharing resonators (hereinafter, the "resonator sharing function"). As a result, phase locking is achieved with more reliability.

Here, each connection waveguide may be arranged so that an extension direction of the connection waveguide crosses extension directions of the at least two adjacent light waveguides.

Also, end parts of each connection waveguide may be bent so that the connection waveguide smoothly merges with the at least two adjacent light waveguides.

This construction reduces the amounts of lights that are scattered and lost at connections between the connection waveguides and the light waveguides.

The first object of the present invention is also achieved by a semiconductor laser array apparatus including: a substrate; a plurality of current blocking elements that are formed on the substrate; and a plurality of light waveguides that are formed between the plurality of current blocking elements, where at least two adjacent light waveguides are bent and connected via at least one point.

This construction allows the semiconductor laser array apparatus to match emitted laser lights in wavelength and phase (phase locking is achieved) without arranging semiconductor laser elements close to each other in the width direction thereof on the same substrate.

Also, with the technique of the present invention, semiconductor laser elements are not arranged close to each other in the width direction thereof on the same substrate. This increases design flexibility and reduces the amount of heat generated at each laser element. As a result, the reliability of the apparatus is increased.

Further, because semiconductor laser elements are not arranged close to each other on the same substrate, the technique of the present invention provides phase locking with reliability, in comparison with the conventional technique. That is, with the conventional technique where phase locking is achieved by arranging semiconductor laser elements close to each other, the phase locking cannot be achieved with reliability due to the unevenness of the distribution of each laser light in a horizontal direction. However, with the technique of the present invention where light waveguides are connected to each other and resonators are partially shared, phase locking is achieved with reliability by the light interference function and the resonator sharing function.

The first object of the present invention is further achieved by a semiconductor laser array apparatus including: a substrate that includes a first end face and a second end face opposing to each other; a current blocking element that is formed on the substrate, first grooves and second grooves being formed in the current blocking element, the first grooves extending in parallel from the first end face toward the second end face, and the second grooves extending in parallel from the second end face toward the first end face; first light waveguides that are respectively formed in the first grooves; and second light waveguides that are respectively formed in the second grooves, where the first and second light waveguides are alternatively arranged in an arrangement direction thereof.

This construction allows the semiconductor laser array apparatus to cause interference between emitted laser lights and to match the laser lights in wavelength and phase (phase locking is achieved) without arranging semiconductor laser elements close to each other in the width direction thereof on the same substrate.

Because this construction provides phase locking by causing interference between laser lights, the ends of opposing waveguides need to be arranged close to each other in the extension direction of the waveguides to obtain overlapping waveguide areas through which lights seep. However, unlike the conventional technique, the waveguides are not arranged close to each other in an arrangement direction of the waveguides. That is, the technique of the present invention provides phase locking with a construction that differs entirely from that of the conventional technique.

Here, the semiconductor laser array apparatus may further include: a p-type sheet electrode; and an n-type sheet electrode, where the plurality of current blocking elements and the light waveguides are sandwiched between the p-type sheet electrode and the n-type sheet electrode.

Also, the semiconductor laser array apparatus may further include: a window-mirror structure that is established at each end part of the apparatus that includes end parts of the light waveguides.

With this construction, the amounts of laser lights absorbed into the end parts of the waveguides are reduced and the amount of generated heat is decreased.

Here, the semiconductor laser array apparatus may further include: an insulating part that is formed at each area where an electric power is applied to a surface of the window-mirror structure.

This construction further decreases the amount of heat generated at the end parts of the waveguides.

Here, a forbidden band width of each current blocking element may be larger than a forbidden band width of an active layer of each light waveguide, and a refractive index of each current blocking element may be smaller than a refractive index of each light waveguide.

This construction improves laser characteristics and, for instance, reduces a threshold current value. Also, this construction makes it possible to extend waveguide areas by decreasing the amounts of laser lights absorbed into the current blocking layer. Therefore, laser lights are optically connected to each other merely by arranging the light waveguides so that their waveguide areas overlap each other. That is, it is not necessary to arrange the waveguides in close proximity to each other in the extension direction or the width direction.

The second object of the present invention is achieved by a multi-wavelength laser light emitting apparatus including: a plurality of semiconductor laser array apparatuses, each of which emits a laser light of a different wavelength; and an optical component that condenses each emitted laser light at a predetermined point, where at least one of the plurality of semiconductor laser array apparatuses includes a laser array structure where a plurality of light waveguides are formed between a plurality of current blocking elements, and at least two adjacent light waveguides are optically connected to each other.

Here, the multi-wavelength laser light emitting apparatus may further include: an adjusting unit for displacing the optical component to condense each emitted laser light at the predetermined point; a laser driving unit for selecting and exciting a semiconductor laser array apparatus that emits a laser light of a specified wavelength; and a control unit for controlling the adjusting unit according to the specified wavelength.

Here, each of the plurality of semiconductor laser array apparatuses may include: a substrate; a plurality of current blocking elements that are stripe shaped and are formed on the substrate; and a plurality of light waveguides that are formed between the plurality of current blocking elements, where at least two adjacent light waveguides are optically connected by removing a part of each current blocking element therebetween.

Here, each of the plurality of semiconductor laser array apparatuses may include: a substrate; a plurality of current blocking elements that are formed on the substrate; and a plurality of light waveguides that are formed between the plurality of current blocking elements, where at least two adjacent light waveguides are bent and connected via at least one point.

Here, each of the plurality of semiconductor laser array apparatuses may include: a substrate that includes a first end face and a second end face opposing to each other; a current blocking element that is formed on the substrate, first grooves and second grooves being formed in the current blocking element, the first grooves extending in parallel from the first end face toward the second end face, and the second grooves extending in parallel from the second end face toward the first end face; first light waveguides that are respectively formed in the first grooves; and second light waveguides that are respectively formed in the second grooves, where the first and second light waveguides are alternatively arranged in an arrangement direction thereof.

BRIEF DESCRIPTION OF THE DRAWINGS

These and other objects, advantages and features of the invention will become apparent from the following description thereof taken in conjunction with the accompanying drawings which illustrate a specific embodiment of the invention. In the drawings.

DESCRIPTION OF THE PREFERRED EMBODIMENTS

Embodiments of the present invention are described below with reference to the drawings.

<First Embodiment>

Figure 1:
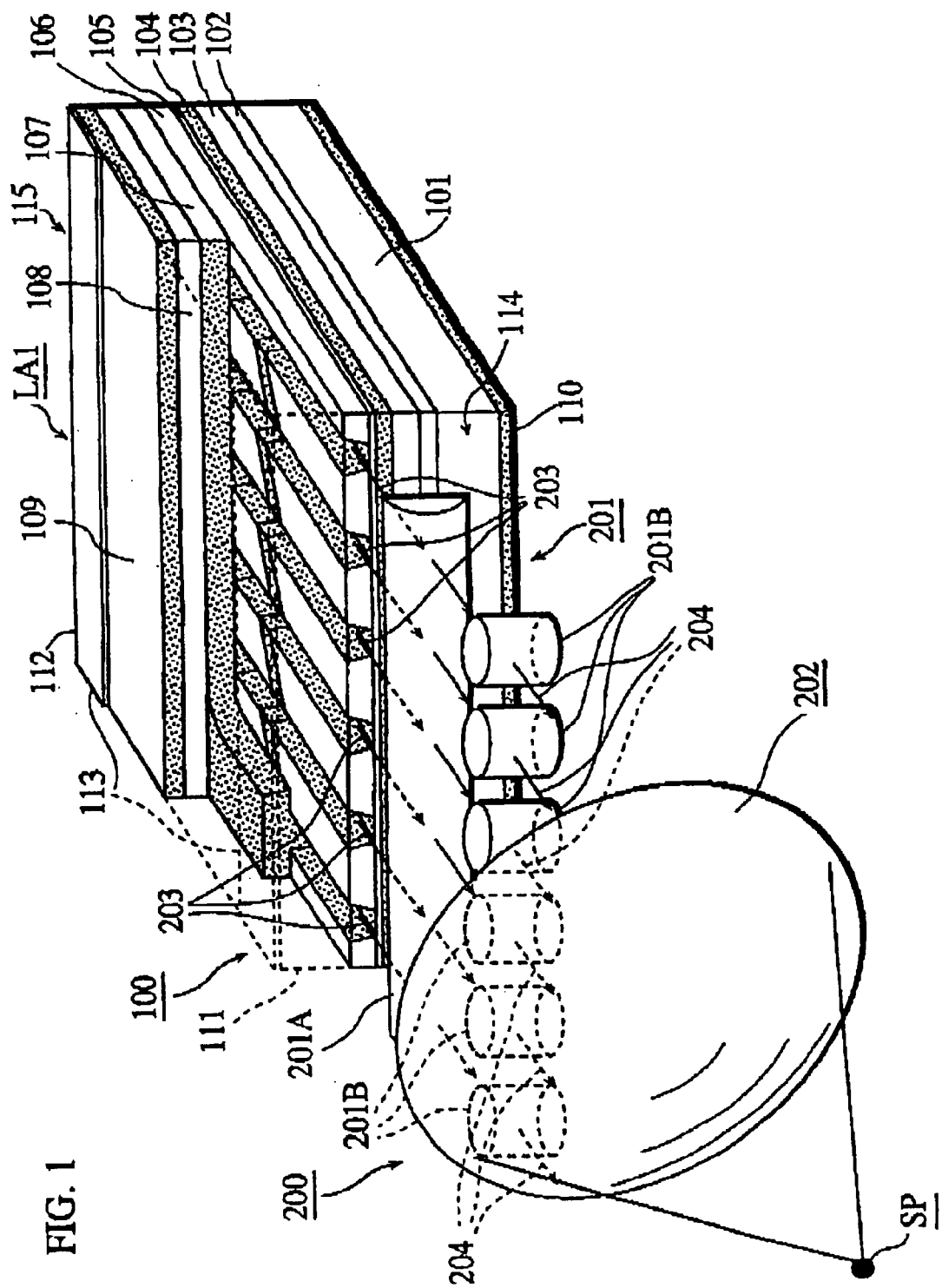
FIG. 1 is a perspective view showing the construction of a semiconductor laser array apparatus of the first embodiment.

FIG. 1 is a perspective view showing the construction of a semiconductor laser array apparatus LA1 of the first embodiment.

<Overview of Construction>

The semiconductor laser array apparatus LA1 includes a semiconductor laser array component 100 and an optical system 200. The semiconductor laser array component 100 includes a plurality of laser oscillation units arranged on the same substrate, and the optical system 200 condenses laser lights emitted from the laser oscillation units to form a spot.

The semiconductor laser array component 100 is an array structure that includes a plurality of red semiconductor laser elements and has an real refractive index waveguide structure. More specifically, an n-type GaAs substrate 101, an n-type GaAs buffer layer 102, an n-type AlGaInP cladding layer 103, a GaInP/AlGaInP quantum well-structured active layer 104, a p-type AlGaInP cladding base layer 105, an n-type AlInP current blocking layer 106, a p-type AlGaInP buried cladding layer 107, and a p-type GaAs capping layer (heatsink) 108 are laminated in this order. A Cr/Pt/Au three-layered p-type sheet electrode 109 is formed on the upper surface of the p-type GaAs capping layer 108 and an AuGe/Ni/Au three-layered n-type sheet electrode 110 is formed on the lower surface of the n-type substrate 101.

The optical system 200 includes a parallel ray generating unit 201 for generating parallel rays and a condenser lens 202. The parallel ray generating unit 201 includes collimator lenses 201A and 201B for converting a plurality of laser lights 203 emitted from the semiconductor laser array component 100 into a plurality of parallel rays. The condenser lens 202 receives the parallel rays 204 from the parallel ray generating unit 201 and condenses them into a spot SP. To prevent phase shifts, it is preferred that the condenser lens 202 is designed to correct the optical path differences of the parallel rays 204 while condensing the parallel rays.

<Details of Construction>

Details of the stated construction elements, such as the n-type AlInP current blocking layer 106 and the p-type AlGaInP buried cladding layer 107, are described below.

Figure 2:
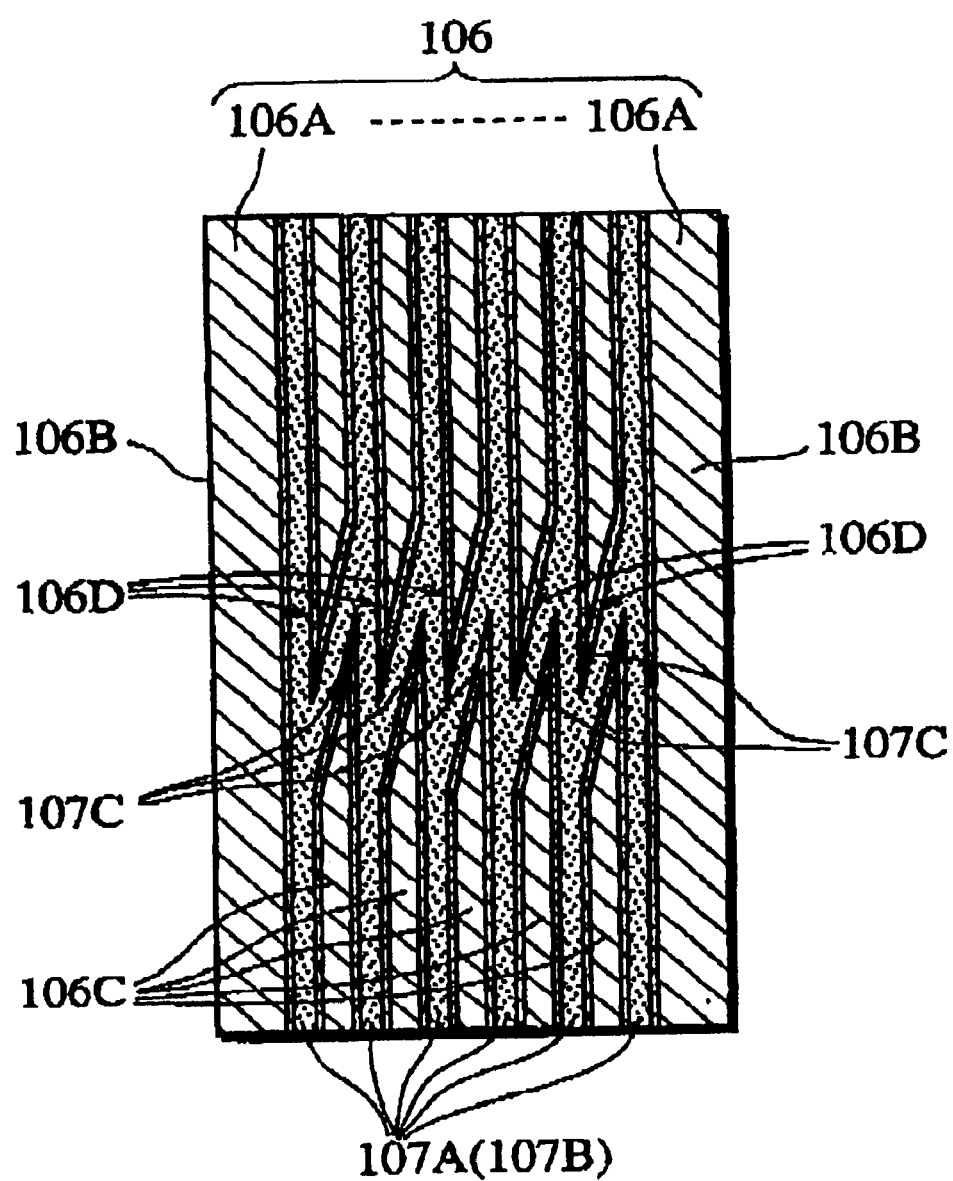
FIG. 2 is an internal view from above of a semiconductor laser array component of the semiconductor laser array apparatus.

FIG. 2 is an internal view from above of the semiconductor laser array component shown in FIG. 1.

As shown in this drawing, the n-type AlInP current blocking layer 106 includes a plurality of stripes 106A that are formed on the p-type AlGaInP cladding base layer 105 at certain intervals.

The p-type AlGaInP buried cladding layer 107 covers the current blocking layer and is buried in grooves between the stripes 106A.

The stripes 106A are divided into two groups: stripes 106B at both ends of the current blocking layer 106, and stripes 106C other than the stripes 106B. As shown in this drawing, the center area (in an extension direction) of each stripe 106C is removed to form a discontiguous area 106D that is inclined with reference to the extension direction.

The p-type AlGaInP buried cladding layer 107 is also buried in the discontiguous areas 106D to form connection waveguides 107C that optically and physically connect adjacent p-type AlGaInP buried cladding layer areas 107A.

The p-type AlGaInP buried cladding layer areas 107A function as current channels and form a pn junction with the active layer therebelow. Also, each p-type AlGaInP buried cladding layer area 107A forms a laser light waveguide (hereinafter referred to as the "main waveguide 107B"). Also, the connection waveguides 107C in the discontiguous areas also function as current channels and form an pn junction with the active layer therebelow. With this construction, the connection waveguides 107C and the main waveguides 107B are optically connected to each other.

Also, as shown in FIG. 1, a window-mirror structure is established by forming Zn diffused areas 111 and 112 on the external surface of the semiconductor laser array component 100. The Zn diffused areas 111 and 112 are formed by diffusing Zn so that the areas 111 and 112 cover both end surface areas of the p-type electrode and surface areas exposed to waveguide areas corresponding to at least (1) both end parts of the main waveguides and (2) vicinities of the end parts. With this construction, the amounts of laser lights absorbed into the end parts of the main waveguides are reduced and the temperature of the semiconductor laser array apparatus LA1 remains relatively low.

An $SiO_2$ insulating layer 113 is further formed on the Zn diffused areas 111 and 112 on the p-type electrode 109. This construction eliminates the necessity to supply power to the end faces 114 and 115 and thus further reduces the amount of heat generated at these faces. It should be noted here that the Zn diffused areas 111 and 112 may be extended to also cover the n-type electrode and an $SiO_2$ insulating layer may be provided on the Zn diffused areas covering the n-type electrode. Here, materials are selected so that the forbidden band width of the current blocking layer becomes larger than that of the active layer and the refractive index of the current blocking layer becomes smaller than that of the p-type buried cladding layer. Therefore, in this embodiment, the p-type cladding base layer is made of AlGaInP and the current blocking layer is made of AlInP. This reduces the amount of laser light absorbed into the current blocking layer and lights are efficiently confined by the difference between effective refractive indexes, which reduces laser light loss.

Note that although not shown in the drawings, the end face 114 emits laser lights but the end face 115 does not emit laser lights. Therefore, a layer having a low reflection coefficient of the order of 1–15% is formed on the end face 114 and a layer having a high reflection coefficient of the order of 70–98% is formed on the end face 115. The low-reflection-coefficient layer is made of a material, such as $Al_2O_3$, $SiO_2$, $Si_3N_4$, and $TiO_2$, with a certain method. Also, the high-reflection-coefficient layer is formed with a certain method. For instance, this high-reflection-coefficient layer is formed by alternately laminating low-refractive-index dielectric layers and high-refractive-index dielectric layers. In this case, the high-reflection-coefficient layer is composed of at least one low-refractive-index dielectric layer and at least one high-refractive-index dielectric layer. The low-refractive-index dielectric layer is made of a material, such as $Al_2O_3$, $SiO_2$, or $Si_3N_4$, and the high-refractive-index dielectric layer is made of a material, such as $TiO_2$, amorphous Si, and amorphous silicon hydroxide.

<Manufacturing Method of Semiconductor Laser Array Component 100>

Figure 3:
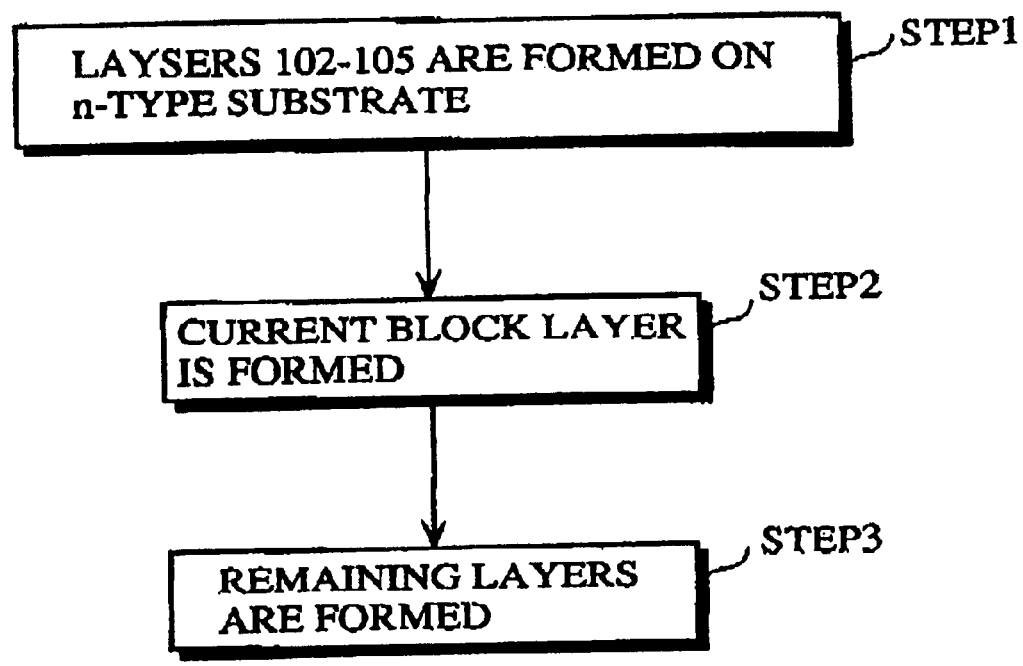
FIG. 3 shows the process of manufacturing the semiconductor laser array component.

FIG. 3 shows the process of manufacturing the semiconductor laser array component 100.

Each construction element other than the n-type GaAs substrate is sequentially formed with a metal organic vapor phase epitaxy method (hereinafter referred to as the "MOVPE method"). More specifically, layers 102–105 are formed on the n-type substrate in this order (step 1). Then the n-type AlInP current blocking layer 106 is formed on the p-type cladding base layer 105 (step 2). The current blocking layer 106 is formed by producing an AlInP layer and subjecting the layer to liquid phase etching using a mask of a predetermined pattern. Following this, the remaining layers 107 and 108 are formed in this order with the MOVPE method (step 3).

Figure 4:
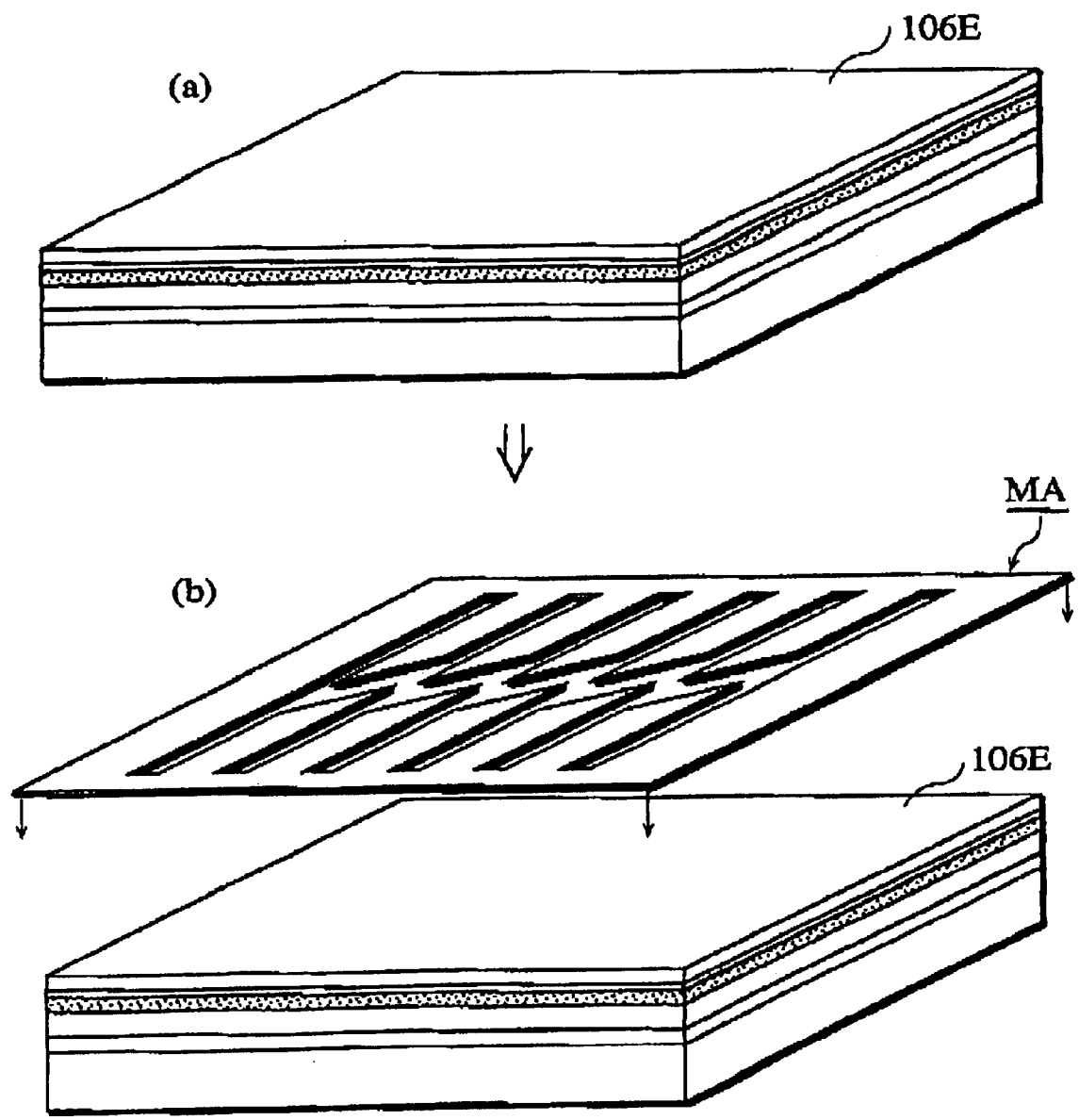
FIGS. 4A and 4B illustrate the detailed process of forming an n-type AlInP current blocking layer.

FIGS. 4A and 4B illustrate the detailed process in step 2 where the n-type AlInP current blocking layer 106 is formed.

First, as shown in FIG. 4A, an AlInP layer 106E is formed on the p-type AlGaUnP cladding base layer 105.

Then, as shown in FIG. 4B, a mask MA of a predetermined pattern is formed to be in tight contact with the layer 106E using a photolithography method, and liquid phase etching is performed from above of the mask MA to form the predetermined pattern in the layer 106E.

In this manner, the n-type AlInP current blocking layer 106 having the predetermined pattern is formed.

<Function and Effect of Semiconductor Laser Array Apparatus LA1>

The semiconductor laser array apparatus LA1 having the stated construction has a function (described in detail later) of producing resonance of laser lights in adjacent main waveguides 107B. Therefore, the laser lights are matched in wavelength and phase (phase locked) without arranging the main waveguides close to each other on the substrate. This prevents a situation where laser lights condensed into a laser spot interfere with each other and cancel each other out due to phase shifts. As a result, the output power of the semiconductor laser array apparatus LA1 is increased in accordance with the number of laser oscillation units.

Also, because the present semiconductor laser array apparatus LA1 does not adopt a technique where laser elements are arranged close to each other on the same substrate, the amount of heat generated at each laser element is reduced.

Further, because it is unnecessary to arrange the laser elements close to each other on the same substrate, the flexibility in designing the semiconductor laser array apparatus LA1 is increased.

Figure 5:
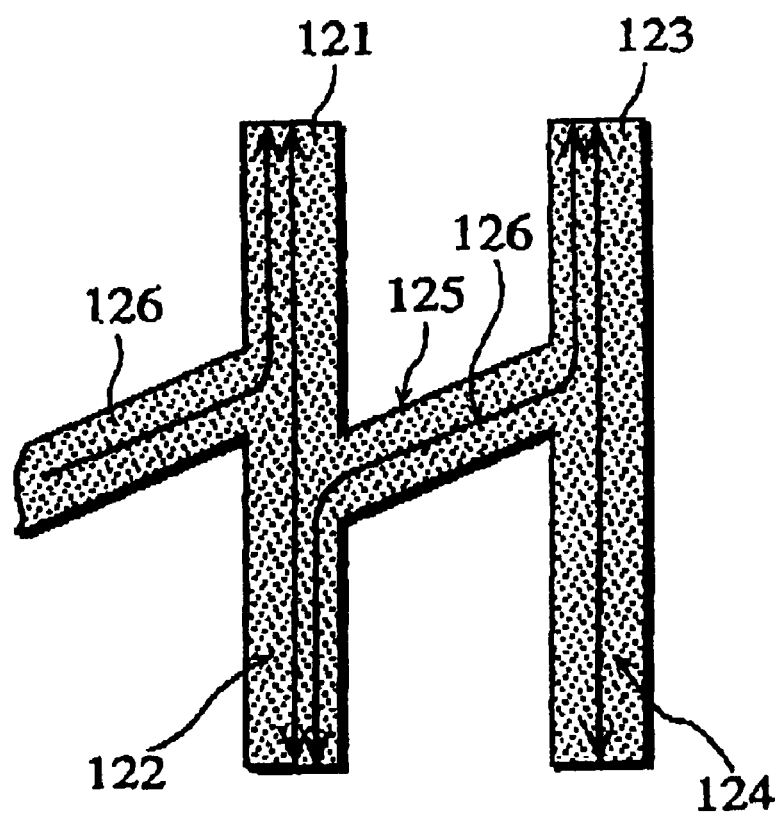
FIG. 5 illustrates a resonator sharing function of the semiconductor laser array component.

FIG. 5 illustrates the stated function (a function of sharing resonators) in detail.

As described above, the main waveguides 107B are connected to each other by the connection waveguides 107C, which means that resonators are shared.

More specifically, a resonator 122 is formed by a main waveguide 121 in an extension direction of the main waveguide 121 and a resonator 124 is formed by another main waveguide 123 in an extension direction of the main waveguide 123. Because these resonators 122 and 124 are connected to each other by a connection waveguide 125, a resonator 126 is additionally formed by the connection waveguide 125 and parts of the resonators 122 and 124.

This causes the interference between lights traveling through the main waveguides 121 and 123 adjacent to each other. Also, as described above, the resonator 126 is additionally formed between the main waveguides 121 and 123. Consequently, laser lights in these main waveguides are matched in wavelength and phase and phase locking occurs with stability and reliability.

Because phase locking occurs between adjacent main waveguides, phase locking also occurs across a plurality of main waveguides.

<Angle of Connection Waveguide>

One important thing for the stated construction where resonators are shared between adjacent main waveguides is the angle between the extension direction of the connection waveguides and that of the main waveguides.

That is, if the connection waveguides are formed perpendicular to the main waveguides, large amounts of lights are scattered and lost at connections between the connection waveguides and the main waveguides. However, if the connection waveguides are inclined with reference to the extension direction of the main waveguides, the amounts of lights scattered and lost at the connections are reduced and resonators are efficiently shared between adjacent main waveguides.

Figure 6:
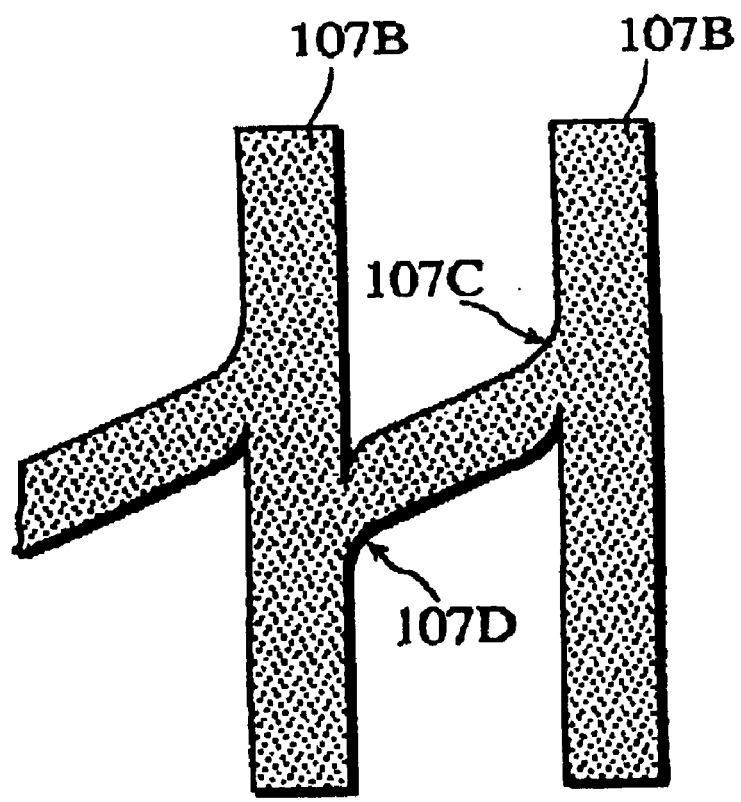
FIG. 6 shows a preferred angle between a connection waveguide and main waveguides.

Accordingly, it is preferred that the connection waveguides include bends in the vicinities of connections with the main waveguides (see bends 107D shown in FIG. 6).

For the efficient sharing of resonators, it is also preferred that the connection waveguides completely cross the main waveguides.

<Variations of Connection Waveguide>

(1) In the above embodiment, a single connection waveguide is formed in each space between the main waveguides. However, the present invention is not limited to this and a plurality of connection waveguides may formed in each space between the main waveguides.

Figure 7:
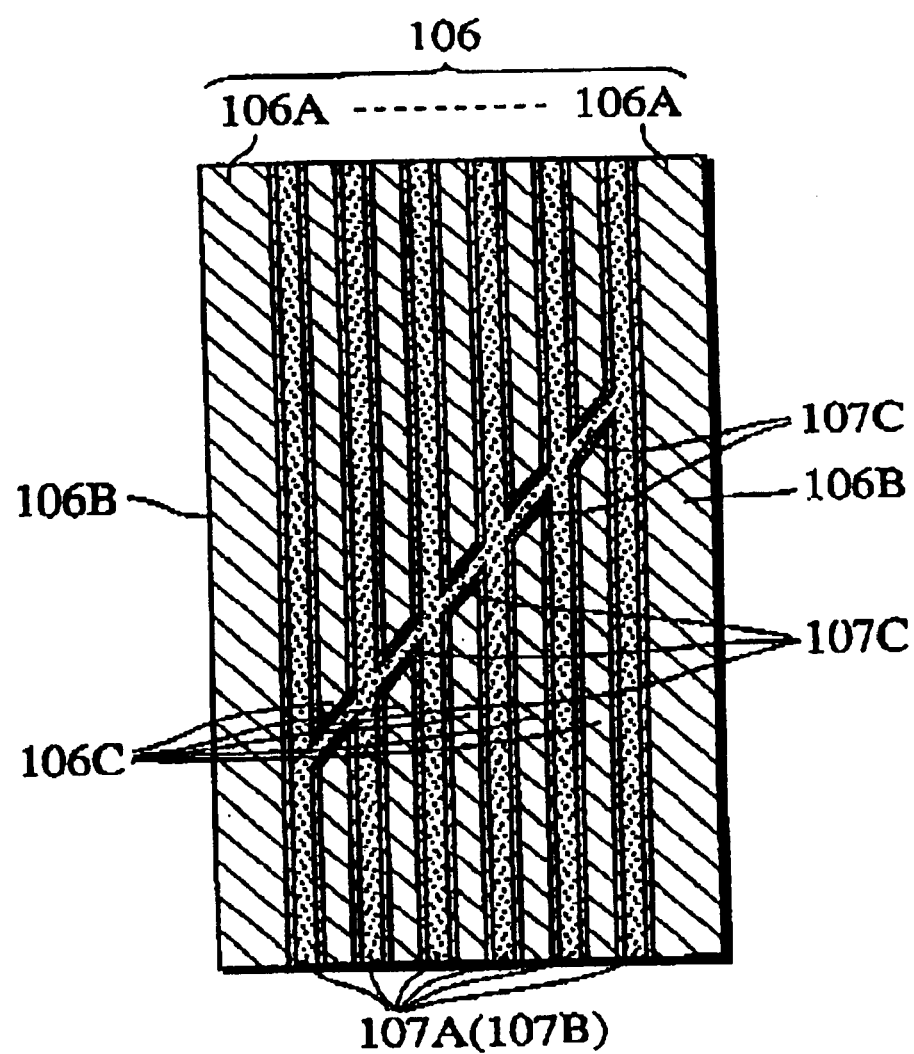
FIG. 7 shows a variation of the connection waveguide.

(2) Also, in the embodiment, the connection waveguides are connected to the center areas of the main waveguides. However, as shown in FIG. 7, the connection waveguides may be arranged in a straight line crossing the main waveguides in a slanting direction. This construction allows all of the main waveguides to be shared and thus provides more stable and reliable phase locking.

(3) Further, in the embodiment, all of the main waveguides are connected to their adjacent main waveguides by the connection waveguides. However, the present invention is not limited to this and includes a construction where at least two of the main waveguides are connected to each other.

In this case, to provide phase locking, the main waveguides that are not connected to each other need to be arranged so that waveguide areas of them partially contact or overlap each other.

If laser elements are arranged close to each other on the same substrate, the amount of heat generated at each laser element usually becomes large. However, because the main waveguides are only partially close to each other in this case, the amount of heat generated at each laser element becomes small in comparison with a conventional technique where entire parts of the laser elements are close to each other.

(4) Also, in the embodiment, laser lights traveling through the main waveguides are coupled with each other by the connection waveguides that completely cross the current blocking layer in a width direction of the current blocking layer and establishes the physical connections between the main waveguides. However, even if the main waveguides are not physically connected, phase locking may be achieved. To do so, the current blocking layer is partially removed to obtain discontiguous areas and laser lights traveling through the main waveguides are optically coupled with each other by the discontiguous areas. It should be noted here that to provide phase locking with more reliability, it is preferred that the main waveguides are connected physically as well as optically, like in the embodiment.

<Second Embodiment>

A semiconductor laser array apparatus LA2 of the present embodiment includes an n-type AlInP current blocking layer 300 that differs from the current blocking layer 106 of the first embodiment in shape. Other construction elements of the semiconductor laser array apparatus LA2 are the same as those of the semiconductor laser array apparatus LA1. The following description centers on the differences between these apparatuses LA1 and LA2.

Figure 8:
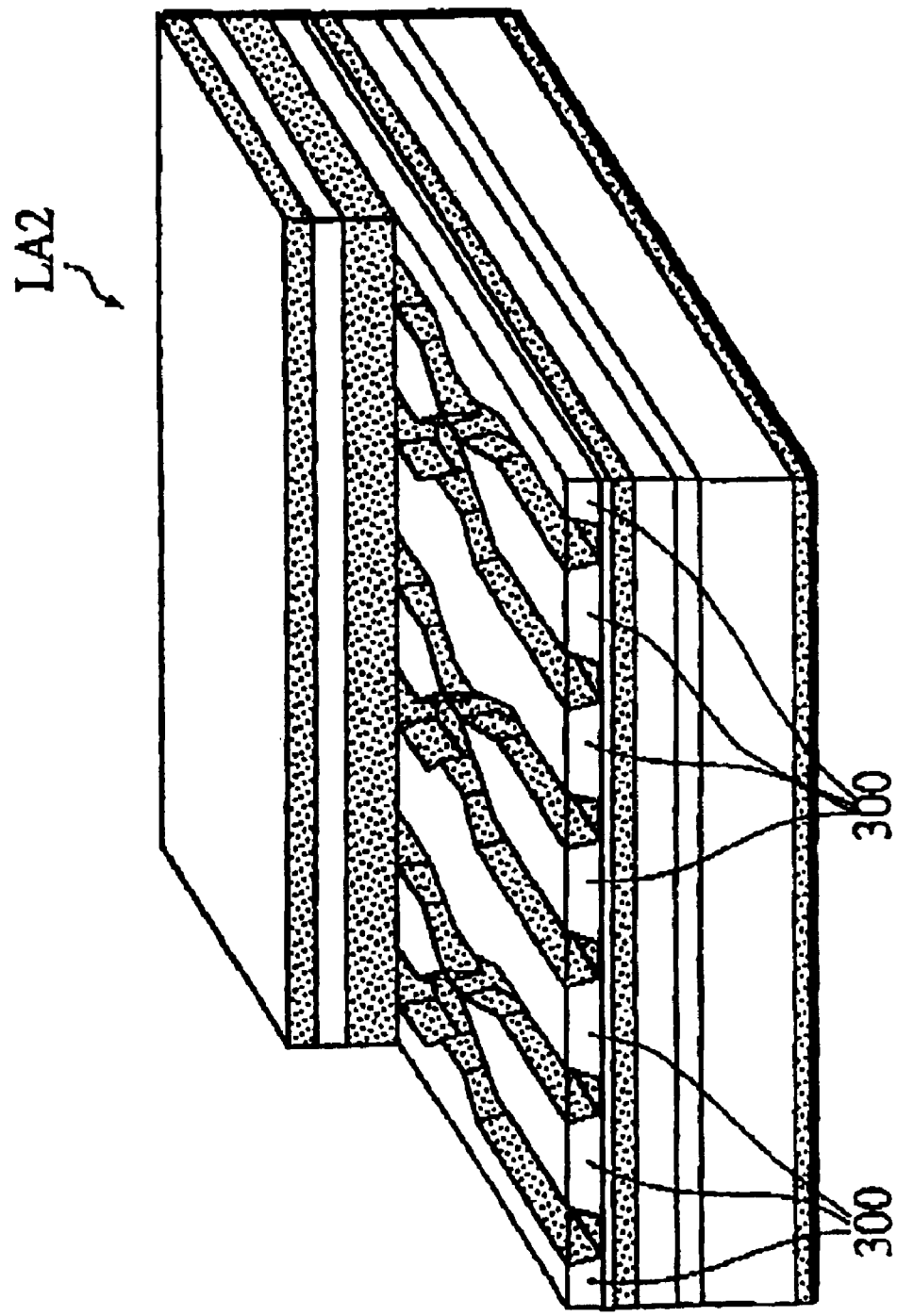
FIG. 8 is a perspective view showing the construction of a semiconductor laser array component of a semiconductor laser array apparatus of the second embodiment.
Figure 9:
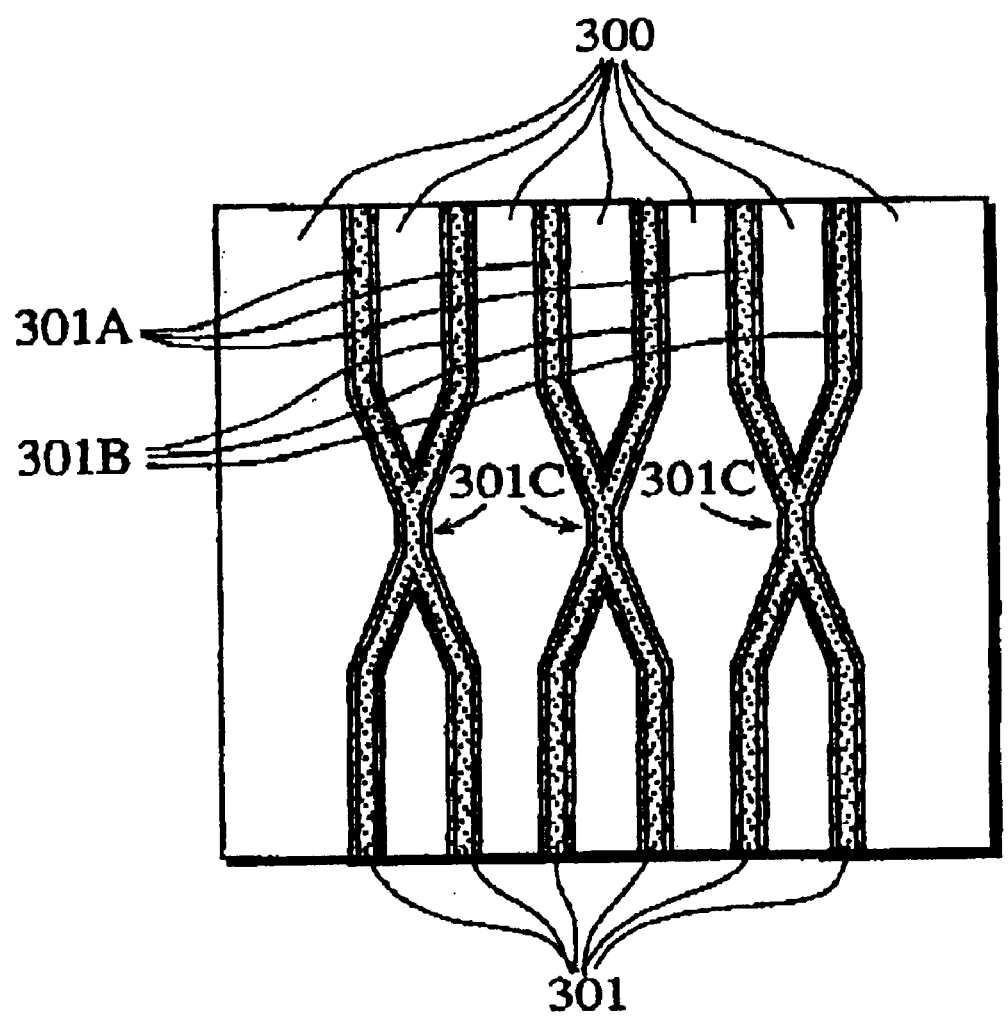
FIG. 9 is an internal view from above of the semiconductor laser array component of the second embodiment.

FIG. 8 is a perspective view showing the construction of a semiconductor laser array component of the semiconductor laser array apparatus LA2. FIG. 9 is an internal view from above of the semiconductor laser array component shown in FIG. 8.

As shown in FIG. 9, the current blocking layer 300 has a construction where discontiguous areas of the current blocking layer 300 are bent to form a plurality of pairs of waveguides in an X-letter shape. With this construction, waveguides are connected with their adjacent waveguides.

More specifically, the n-type AlInP current blocking layer 300 is composed of a plurality of current block areas, between which waveguides 301 are formed by a p-type buried cladding layer. The waveguide 301 are connected to their adjacent waveguides at their centers. Therefore, when viewed from above, each pair of adjacent waveguides has the shape of the letter "X". The waveguides 301 formed in the discontiguous areas are hereinafter referred to as the "X junction waveguides 301".

With the X junction waveguides 301, lights in each pair of a waveguide 301A (on the left) and a waveguide 301B (on the right) interfere with each other at the junction and resonators are partially shared.

If a plurality of pairs of waveguides 301A and waveguides 301B are formed, interference of lights can be caused even between adjacent waveguides 301 that are not connected to each other. To achieve this effect, the adjacent waveguides 301 are arranged so that their waveguide areas (through which lights seep toward the current blocking layer) partially contact or overlap each other.

With this construction, laser lights in the waveguides 301 are matched in wavelength and phase (the laser lights are phase locked) and a situation is avoided where laser lights condensed into a laser spot interfere with each other and cancel each other out due to phase shifts. As a result, the output power of the semiconductor laser array apparatus LA2 is increased in accordance with the number of laser oscillation units.

Also, because entire parts of the laser elements are arranged close to each other in this embodiment, the amount of heat generated at each laser element becomes small in comparison with a conventional technique where entire parts of laser elements are arranged close to each other.

Here, it is preferred that the junction 301C of each waveguide has a width equal to those of remaining parts of the waveguide. This is because if the width of the junction 301C is greater than those of the remaining parts, the light traveling through the waveguide is scattered at the junction 301C, so that multimode lasers are emitted from the semiconductor laser array apparatus LA2 and a high-energy laser spot cannot be obtained.

In this embodiment, some of the waveguides need to be arranged close to each other. However, this applies to the case of three or more waveguides and does not apply to the case of two waveguides. Accordingly, if only two waveguides are formed, laser elements are not arranged close to each other on the same substrate and the amount of heat generated at each laser element is not increased.

Figure 10:
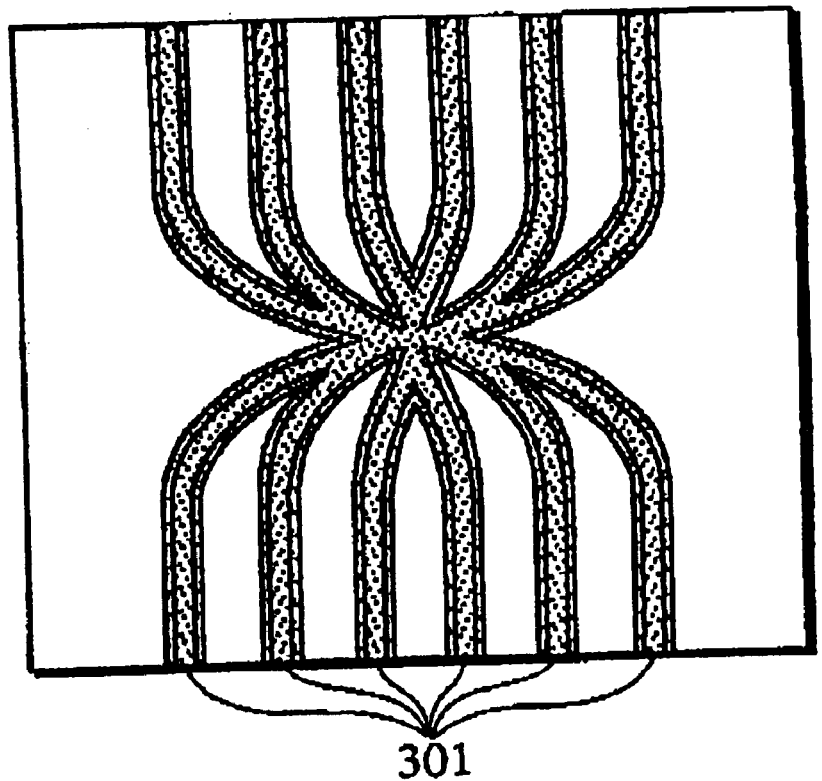
FIG. 10 is an internal view of a semiconductor laser array component of a modified semiconductor laser array apparatus of the second embodiment.

Needless to say, if three or more waveguides are formed, it is possible to connect all of the waveguides via a single junction (see FIG. 10). However, this construction tends to widen the optical path differences between (1) the waveguides in the center area in an arrangement direction of the waveguides and (2) the waveguides at both ends in the arrangement direction. This causes phase differences and hinders the increase in an optical output power. Therefore, if all of a plurality of waveguides are connected via a single junction, optical path differences need to be regulated so that phase differences are not caused.

<Third Embodiment>

A semiconductor laser array apparatus LA3 of the present embodiment includes an n-type AlInP current blocking layer 400 that differs from the current blocking layer 106 in shape. Other construction elements of the semiconductor laser array apparatus LA3 are the same as those of the semiconductor laser array apparatus LA1. The following description centers on the differences between these apparatuses LA1 and LA3.

Figure 11:
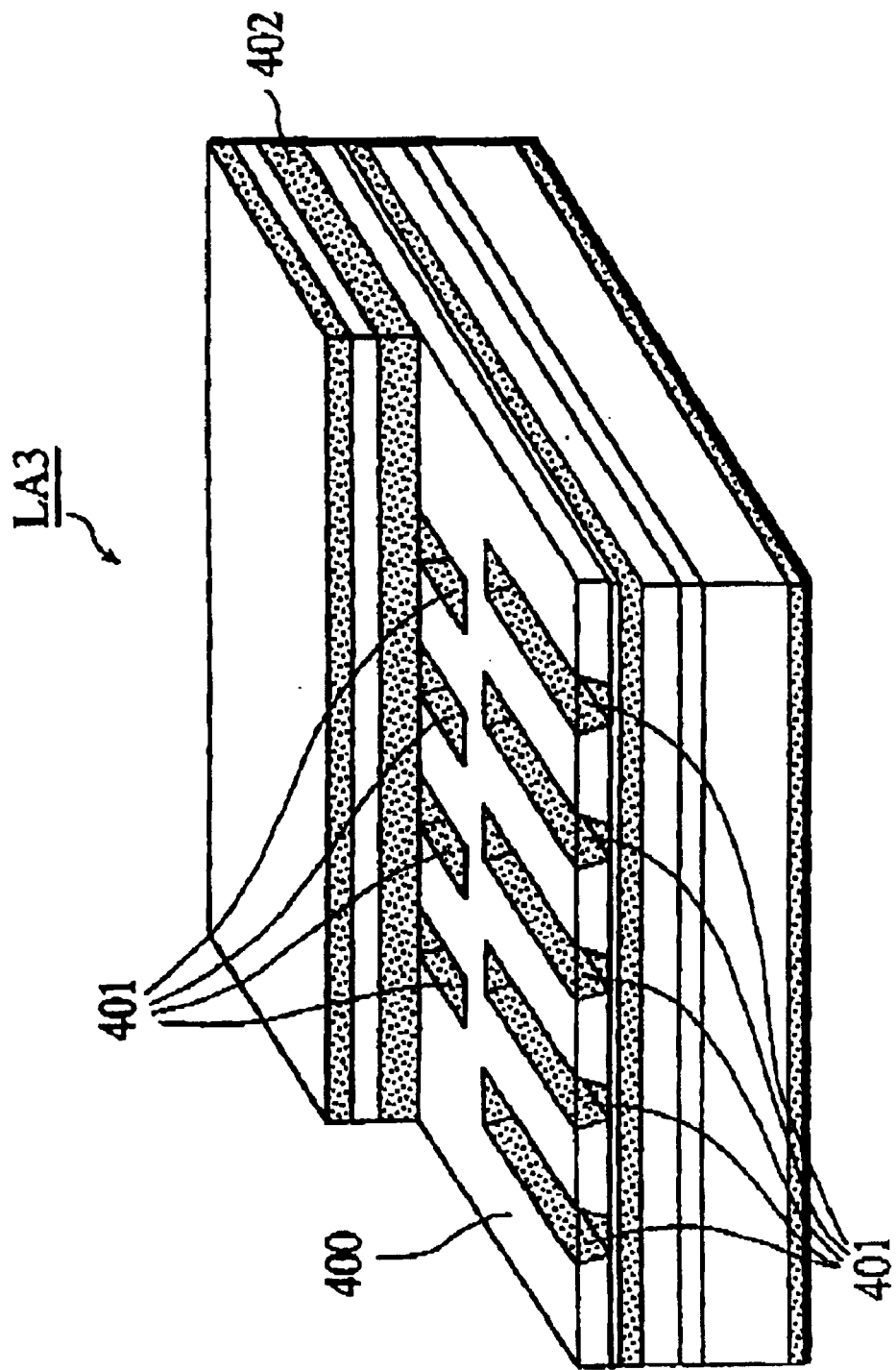
FIG. 11 is a perspective view showing the construction of a semiconductor laser array component of a semiconductor laser array apparatus of the third embodiment.
Figure 12:
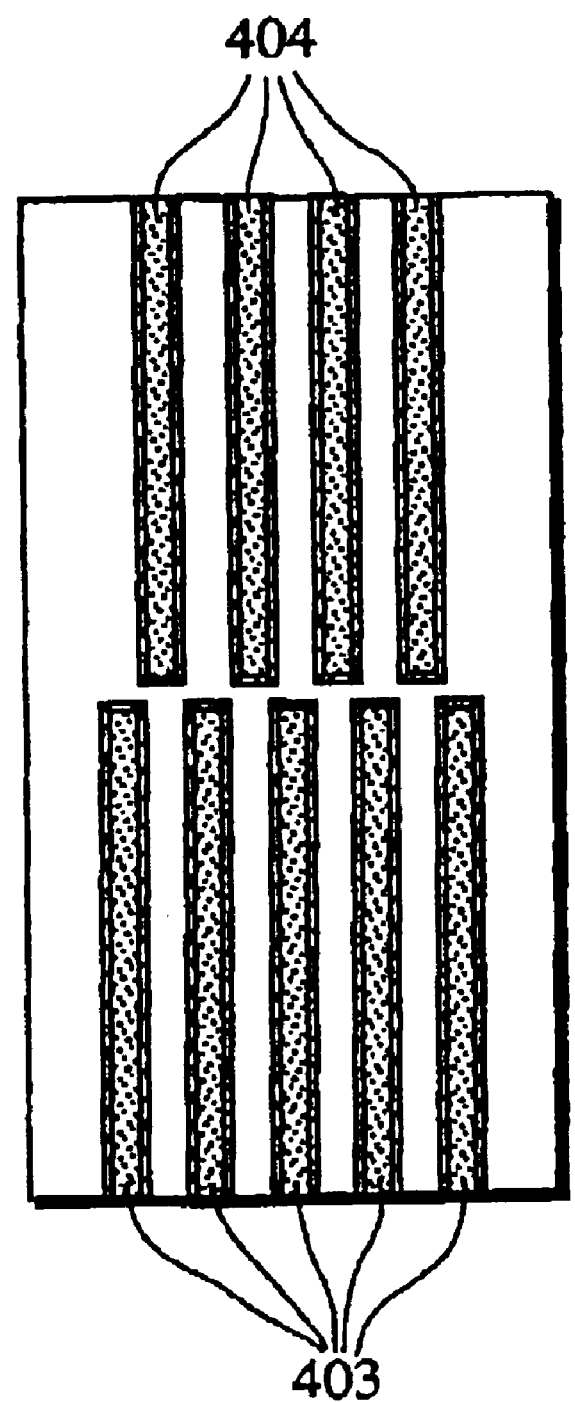
FIG. 12 is an internal view from above of the semiconductor laser array component of the third embodiment.

FIG. 11 is a perspective view showing the construction of a semiconductor laser array component of the semiconductor laser array apparatus LA3. FIG. 12 is an internal view from above of the semiconductor laser array component shown in FIG. 11.

Unlike the n-type AlInP current blocking layer 300 of the second embodiment, the n-type AlInP current blocking layer 400 of the present embodiment is not divided into a plurality of current block areas but has a contiguous single layer surface. A plurality of short grooves 401 extending parallel to each other are formed on the layer surface using a mask of a predetermined pattern. A p-type AlGaInP buried cladding layer 402 is buried in the grooves 401 having the predetermined pattern.

More specifically, the grooves 401 in which the p-type AlGaInP buried cladding layer 402 has been buried (and the mask used to form the grooves 401) includes stripes 403 and stripes 404. The stripes 403 extend parallel to each other from the lower end of the layer 400 to the vicinity of the center area of the layer 400, and the stripes 404 extend parallel to each other from the upper end of the layer 400 to the vicinity of the center area. Here, the stripes 403 and 404 are positioned to have different phases. Also, the distances between the stripes 403 and 404 are regulated so that waveguide areas of these stripes overlap or contact each other (waveguide areas are areas through which lights seep toward the current blocking layer).

This construction allows laser lights confined in the waveguides 403 to interfere with those confined in the waveguides 404, and thus amplifies the confined laser lights. Therefore, laser lights in the waveguides are matched in wavelength and phase (phase locking is achieved) and a situation is avoided where laser lights condensed into a laser spot interfere with each other and cancel each other out due to phase shifts. As a result, the output power of the semiconductor laser array apparatus LA3 is increased in accordance with the number of laser oscillation units.

Although red semiconductor laser elements are used in the embodiments described above, the present invention is not limited to this. That is, blue, green, or infrared semiconductor laser elements may also be used. This construction also produces resonance of laser lights in the waveguides.

<Fourth Embodiment>

The following description concerns an example application for the semiconductor laser array apparatus of the present invention.

Figure 13:
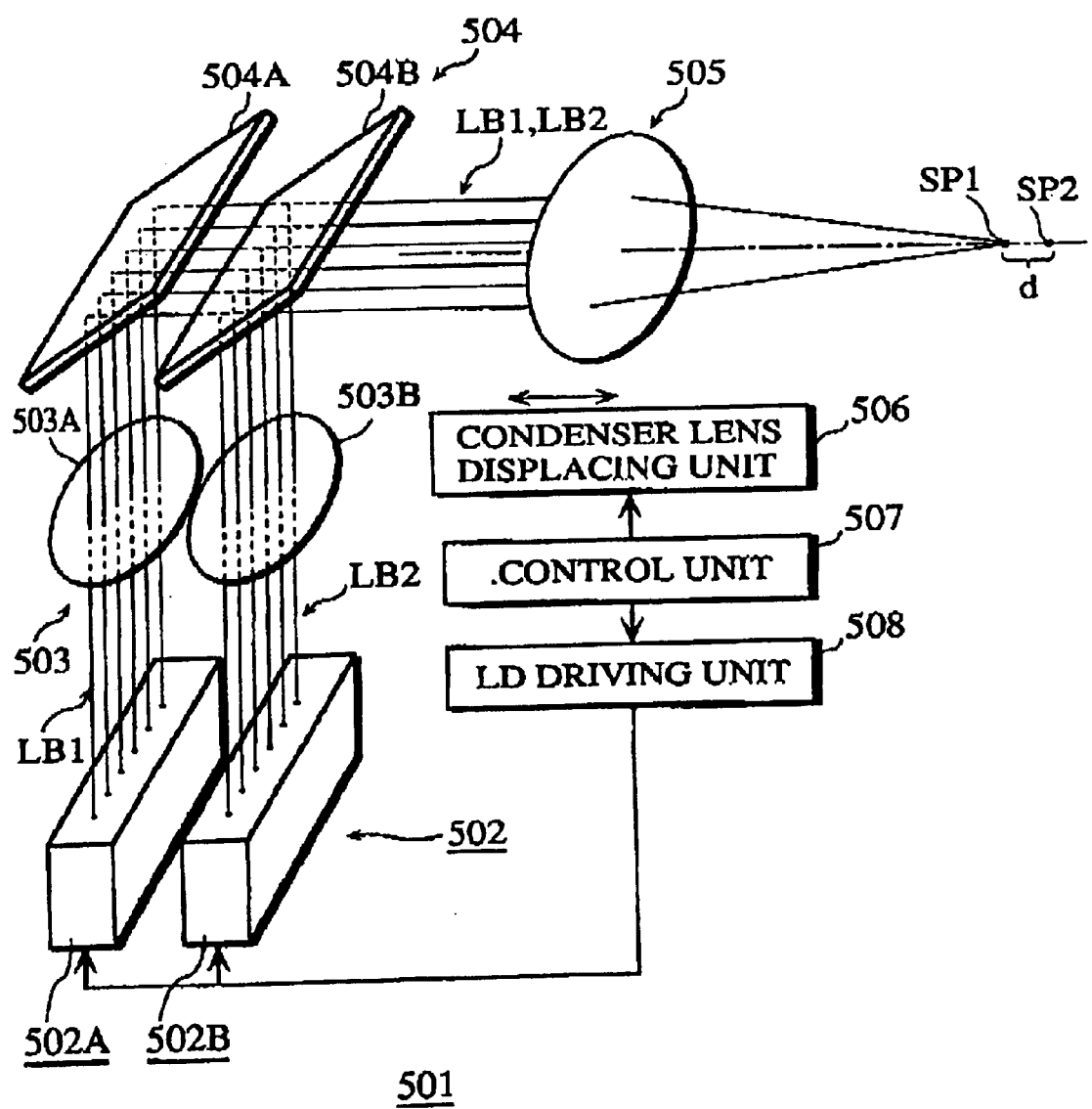
FIG. 13 shows the main construction elements of a multi-wavelength laser emitting apparatus of the fourth embodiment.

FIG. 13 shows the main construction elements of a multi-wavelength laser emitting apparatus 501 of the present embodiment.

As shown in drawing, the multi-wavelength laser emitting apparatus 501 includes a light source unit 502 emitting laser beams LB1 and LB2 of different wavelengths, a collimator unit 503 converting the laser beams LB1 and LB2 into parallel rays, a reflection unit 504 reflecting the parallel rays so that the parallel rays travel parallel to each other in the same direction, a condenser lens 505 condensing the reflected parallel rays into a spot at a predetermined position on its optical axis, a condenser lens displacing unit 506 displacing the condenser lens 505 along the optical axis, and a control unit 507 controlling the operation of the condenser lens displacing unit 506. Note that although a condenser lens is usually composed of a plurality of lenses, the condenser lens 505 includes a single lens in this embodiment.

The light source unit 502 includes semiconductor laser array apparatuses 502A and 502B that are arranged in parallel and emit the parallel laser beams LB1 and the parallel laser beams LB2, respectively. The wavelength of the laser beams LB1 differ from that of the laser beams LB2.

The semiconductor laser array apparatuses 502A and 502B include active layers of different compositions. Therefore, the semiconductor laser array apparatus 502A emits red laser beams and the semiconductor laser array apparatus 502B emits infrared laser beams. Here, each of these semiconductor laser array apparatuses is the semiconductor laser array apparatus of any of the above embodiments and obtains high output powers by emitting phase-locked laser lights LB1 (red) or LB2 (infrared) that are matched in wavelength and phase.

The laser lights LB1 are incident on a hologram optical component 503A and the laser lights LB2 are incident on a hologram optical component 503B. These hologram optical components 503A and 503B are arranged to receive diffused lights from light sources arranged at predetermined positions and convert the diffused lights into parallel rays. As a result, the laser lights LB1 and LB2 are converted into parallel rays by the hologram optical components 503A and 503B. Note that collimator lenses may be used instead of the hologram optical components 503A and 503B.

The reflection unit 504 includes a mirror 504A directing the parallel laser lights LB1 toward the condenser lens 505 and a half mirror 504B directing the parallel laser lights LB2 toward the condenser lens 505. The half mirror 504B is a well-known optical component that receives a light, transmits a part of the light, and reflects another part of the light according to the incident angle of the light. Also, the half mirror 504B is disposed to have an incident angle of 45 degrees to the principal rays of the laser lights LB1 and LB2.

With this construction, the laser lights LB1 reflected by the mirror 504A passes through the half mirror 504B and travels to the condense lens 505 almost parallel to the laser lights LB2 reflected by half mirror 504B. As a result, the laser lights LB1 and LB2 emitted from different positions almost overlap each other and travel in the same direction.

The condenser lens 505 receives the laser lights LB1 and LB2 from the reflection unit 504 and condenses these laser lights into a spot. The spot is formed at a predetermined position (hereinafter referred to as the "spot position") on the optical axis. As well known, however, differences between the wavelengths of incident lights result in differences between spot positions on the optical axis (longitudinal chromatic aberration). As a result, the laser lights LB1 and LB2 are condensed into spots at different points SP1 (red) and SP2 (infrared).

Therefore, in the present embodiment, the condenser lens 505 is displaced along the optical axis according to the wavelength of a currently used laser. This makes it possible to process a work with stability by avoiding a situation where the beam waist positions of laser lights are displaced by the difference in wavelength. That is, the condenser lens 505 is supported in a movable manner and is displaced along the optical axis by the condenser lens displacing unit 506 according to the wavelength of a currently used laser light. This construction keeps the spot points of laser lights constant even if the laser lights have different wavelengths.

When a red laser light is switched to an infrared laser light, for instance, the condenser lens 505 is displaced by a distance "d" (shown in FIG. 13) toward the reflection unit 504 along the optical axis. In this manner, laser lights of different wavelengths are condensed at the same spot point SP1.

The condenser lens displacing unit 506 includes a well-known linear actuator that can perform delicate displacements of the condenser lens 505. The linear actuator is, for instance, a screw sliding system using a ball screw. If the condenser lens 505 includes a plurality of lenses, the condenser lens displacing unit 506 displaces at least one of the plurality of lenses along the optical axis to adjust the spot positions of the laser lights.

The control unit 507 controls the displacement amount of the condenser lens 505 by the condenser lens displacing unit 506, The control unit 507 also controls the light emissions of the semiconductor laser array apparatuses 502A and 502B via the laser diode driving unit 508. More specifically, the control unit 507 switches between the semiconductor laser array apparatuses 502A and 502B to obtain laser lights of a wavelength that is appropriate to a current work. The control unit 507 also prestores displacement amounts of the condenser lens 505 corresponding to the wavelengths of the semiconductor laser array apparatuses 502A and 502B. This ensures that laser lights are condensed at the same spot point regardless of the wavelengths of the laser lights. If a stepping motor is used to drive the condenser lens displacing unit 506, the displacement amounts of the condenser lens 505 can be controlled by the number of driving pulses without difficulty.

Figure 14:
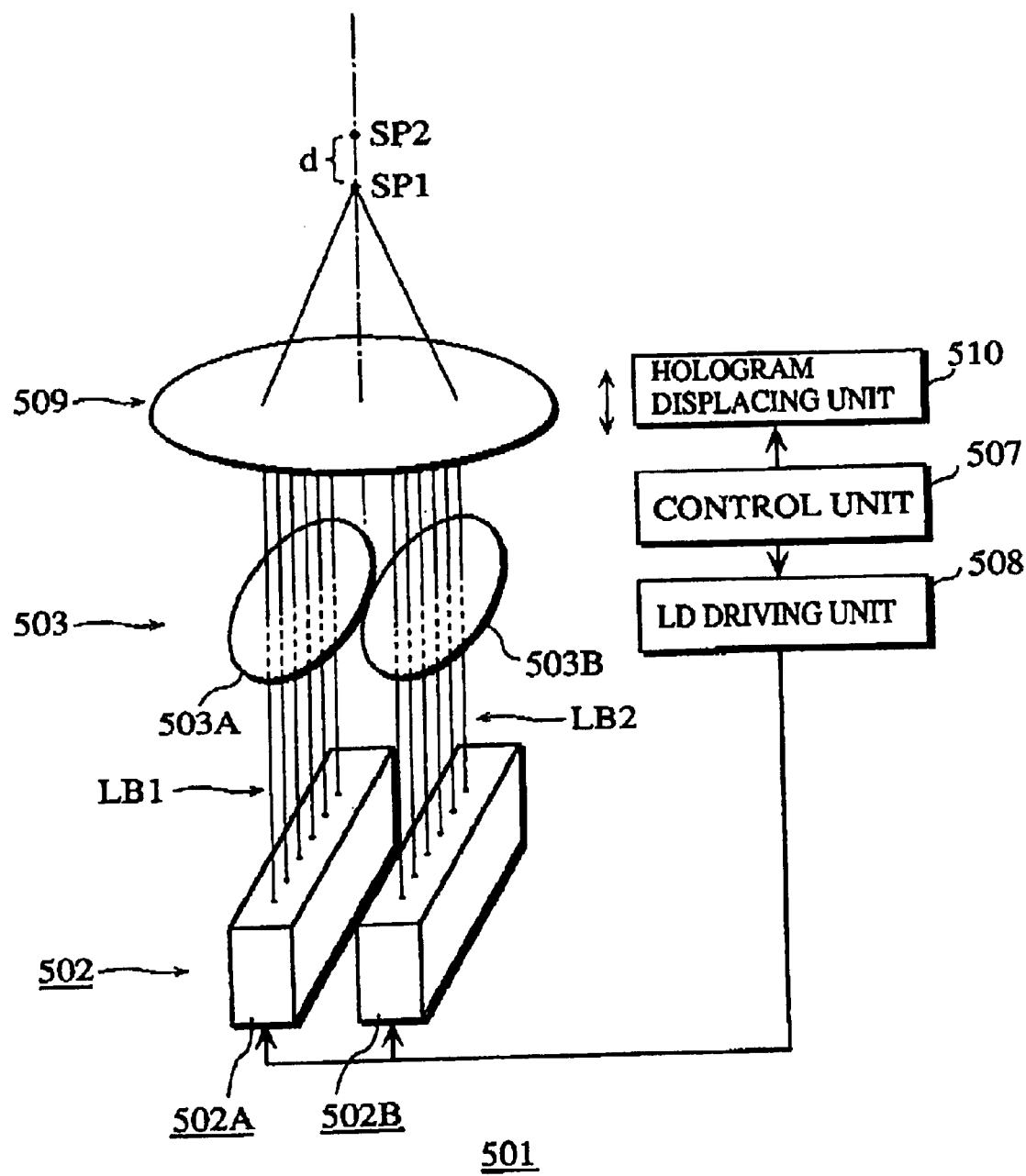
FIG. 14 shows the main construction elements of a modified multi-wavelength laser emitting apparatus of the fourth embodiment.

FIG. 14 shows a modification of the multi-wavelength laser emitting apparatus 501. In this modification, the reflection unit 504 is not used and a hologram optical component 509 is used instead of the condenser lens 505 to condense laser lights. The hologram optical component 509 hardly produces optical distortions even if its diameter is larger than those of lenses 503A and 503B. This makes it unnecessary to have the laser lights LB1 and LB2 travel almost the same optical path using the half mirror 504B shown in FIG. 13, and allows the laser lights LB1 and LB2 to be incident on the hologram optical component 509 without reducing the distance between these laser lights. As a result, the hardware scale of the multi-wavelength laser emitting apparatus 501 is further reduced, the number of parts and the number of assembling steps are reduced, and the cost of the apparatus 501 is suppressed. Also, the halt mirror 504B transmits a part of an incident light and reflects another part of the incident light, as described above. Therefore, the construction shown in FIG. 13 causes enormous losses of laser lights LB1 and LB2. However, the present modification does not use the half mirror 504B, thereby avoiding such losses and reducing power consumption.

Because the construction in this modification cannot avoid longitudinal chromatic aberration caused by the differences between wavelengths of laser lights, the differences between spot points needs to be corrected by displacing the hologram optical component 509 along the optical axis using a hologram displacing unit 510 according to the wavelengths of the laser lights. This displacement is done in a manner similar to that shown in FIG. 13, and so is not described here.

EXAMPLE APPLICATIONS

The following description concerns particularly effective example applications for the semiconductor laser array apparatus of the present invention. Note that the present invention is not limited to the applications below.

(1) Red Laser Made of AlGaInP (Wavelength=655 nm–665 nm)

① The semiconductor laser array apparatus may be incorporated into a welding torch of a welding machine. In this case, because the semiconductor laser array apparatus outputs high-power colored laser lights, visibility is increased and an improvement is made in workability during welding. Also, the semiconductor laser array apparatus may be applied to a punching machine or a cutting machine that punches or cuts a printed board. Further, the semiconductor laser array apparatus may be applied to a surface denaturation processing machine that performs surface denaturation processing, such as so-called hardening.

Also, the semiconductor laser array apparatus may be applied to a weaving process for welding sheet metals (a car body, for instance) by periodically swinging the rod of a robot from side to side. In this case, the weaving can be performed at high speed by incorporating the high-power semiconductor laser array apparatus of the present invention into a welding torch.

② Also, it is effective to use the semiconductor laser array apparatus of the present invention to generate two-dimensional dot matrix data, such as two-dimensional data matrix codes that can be processed with a spot light.

Conventionally, this processing is performed using a YAG laser in usual cases. However, because the responsivity of the YAG laser is low so that it is difficult to form dots evenly at high speed with the YAG laser. For instance, the YAG laser is not suitable for the formation of a matrix pattern where irradiation is intermittently performed by applying short pulses after a long period of idleness. On the other hand, the red semiconductor laser array apparatus has high responsivity and is suitable for such a matrix pattern formation.

(3) Also, the semiconductor laser array apparatus may be applied to a medical equipment used for surgical operations, a laser scalpel for hemostasis, or hair restoration treatment. Further, the semiconductor laser array apparatus may be applied to the treatment of a malignant tumor, such as cancer, by irradiating a living body, into which photofrin has been injected, with laser lights.

(2) Blue Laser Made of InGaN (Wavelength=550 nm, $In_{0.5}Ga_{0.5}N$)

The blue laser may be applied to the treatment of detached retina by irradiating a retina with laser lights.

(3) Green Laser Made of InGaN (Wavelength=380 nm, $In_{0.5}Ga_{0.95}N$)

The green laser may be applied to the treatment of nearsightedness by irradiating a cornea with laser lights.

(4) Infrared Laser Made of InGaAs (Wavelength=1060 nm, $In_{0.2}Ga_{0.9}As$)

In addition to the welding, punching, surface denaturation processing, marking, surgical operations, and laser scalpel for hemostasis, the infrared laser may be applied to the treatment of detached retina by irradiating a retina with laser lights via an SHG element that halves the wavelength of infrared laser lights.

What is claimed is:

1. A multi-wavelength laser light emitting apparatus comprising:

a plurality of semiconductor laser array apparatuses, each of which emits a laser light of a different wavelength; and an optical component that condenses each emitted laser light at a predetermined point, wherein at least one of the plurality of semiconductor laser array apparatuses includes a laser array structure where a plurality of light waveguides are formed between a plurality of current blocking elements, and at least two adjacent light waveguides are optically connected to each other.

2. The multi-wavelength laser light emitting apparatus of claim 1, further comprising:

an adjusting means for displacing the optical component to condense each emitted laser light at the predetermined point;

a laser driving means for selecting and exciting a semiconductor laser array apparatus that emits a laser light of a specified wavelength; and a control means for controlling the adjusting means according to the specified wavelength.

3. The multi-wavelength laser light emitting apparatus of claim 2, wherein each of the plurality of semiconductor laser array apparatuses includes:

a substrate;

a plurality of current blocking elements that are stripe shaped and are formed on the substrate; and a plurality of light waveguides that are formed between the plurality of current blocking elements, wherein at least two adjacent light waveguides are optically connected by removing a part of each current blocking element therebetween.

4. The multi-wavelength laser light emitting apparatus of claim 2, wherein each of the plurality of semiconductor laser array apparatuses includes:

a substrate;

a plurality of current blocking elements that are formed on the substrate; and a plurality of light waveguides that are formed between the plurality of current blocking elements, wherein at least two adjacent light waveguides are bent and connected via at least one point.

5. The multi-wavelength laser light emitting apparatus of claim 2, wherein each of the plurality of semiconductor laser array apparatuses includes:

a substrate that includes a first end face and a second end face opposing to each other;

a current blocking element that is formed on the substrate, first grooves and second grooves being formed in the current blocking element, the first grooves extending in parallel from the first end face toward the second end face, and the second grooves extending in parallel from the second end face toward the first end face;

first light waveguides that are respectively formed in the first grooves; and second light waveguides that are respectively formed in the second grooves, wherein the first and second light waveguides are alternatively arranged in an arrangement direction thereof.

6. The multi-wavelength laser light emitting apparatus of claim 1, wherein more than two light waveguides are arranged in parallel, and further including a single connection waveguide crossing the plurality of parallel waveguides along a straight line which crosses and connects each of the waveguides at a slanted angle.

* * * * *